United States Patent [19]
Dougan et al.

[11] Patent Number: 5,811,105
[45] Date of Patent: *Sep. 22, 1998

[54] VACCINES CONTAINING BACTERIA ATTENUATED BY MUTATIONS IN TWO GENES OF THE AROMATIC AMINO ACID BIOSYNTHETIC PATHWAY

[75] Inventors: Gordon Dougan; Steven Neville Chatfield, both of Beckenham; Carlos Estenio Hormaeche, Cambridge, all of United Kingdom

[73] Assignee: Glaxo Wellcome, Inc., Research Triangle Park, N.C.

[*] Notice: The portion of the term of this patent subsequent to Jun. 23, 2018, has been disclaimed.

[21] Appl. No.: 449,297

[22] Filed: May 24, 1995

Related U.S. Application Data

[62] Division of Ser. No. 135,436, Oct. 13, 1993, abandoned, which is a continuation of Ser. No. 979,460, Nov. 20, 1992, abandoned, which is a continuation of Ser. No. 857,092, Mar. 20, 1992, abandoned, which is a continuation of Ser. No. 642,138, Jan. 15, 1991, abandoned, which is a continuation of Ser. No. 399,539, filed as PCT/GB98/01143, Dec. 22, 1987, abandoned.

[30] Foreign Application Priority Data

Dec. 23, 1987 [GB] United Kingdom ............ 8730037

[51] Int. Cl.$^6$ .................. A61K 39/02; A61K 39/112; C12N 15/00; C12N 1/00
[52] U.S. Cl. .................. 424/235.1; 424/184.1; 424/258.1; 424/278.1; 435/69.3; 435/172.1; 435/172.3; 435/243; 435/245; 435/252.3
[58] Field of Search ............ 424/235.1, 184.1, 424/258.1, 278.1; 435/69.3, 172.1, 172.3, 243, 245, 252.3

[56] References Cited

U.S. PATENT DOCUMENTS

| | | |
|---|---|---|
| 4,337,314 | 6/1982 | Oeschger et al. . |
| 4,535,060 | 8/1985 | Comai . |
| 4,550,081 | 10/1985 | Stocker . |
| 4,681,762 | 7/1987 | Oeschger et al. . |
| 4,735,801 | 4/1988 | Stocker . |
| 4,837,151 | 6/1989 | Stocker . |
| 5,356,797 | 10/1994 | Niesel et al. . |
| 5,527,529 | 6/1996 | Dougan et al. . |
| 5,599,537 | 2/1997 | Miller et al. . |

FOREIGN PATENT DOCUMENTS

| | | |
|---|---|---|
| 0184086 | 6/1986 | European Pat. Off. . |
| WO 80/02504 | 11/1980 | WIPO . |

OTHER PUBLICATIONS

Chemical Abstracts 107, 7, p. 194, 53112x "Isolation of stable aroA mutants of Salmonella . . . ".
Chemical Abstracts 106, 25, p. 497, 212119c "*Salmonella typhimurium* aroA mutants as carriers of . . . ".
Br. J Exper. Path. 32, pp. 85–96, 1951 Bacon et al "The Effects of Biochemical Mutation on the . . . ".

Biological Abstracts 87, 48348 "Construction and Characterization of Vaccine Strains . . . " Dougan et al.

Stocker et al. Vaccine 6, 2, 141–145, Apr. 1988 "Auxotrophic *Salmonella typhi* . . . ".

Collins et al. J. Exp. Med. 124, 601–619, 1966 "Infection–Immunity in Experimental Salmonellosis".

Collins, Bacter. Rev. 38, 371–402, 1974 "Vaccines and Cell–Mediated Immunity".

Maskell et al., Microb. Pathog. 2, 211–221, 1987 "*Salmonella typhimurium* aroA Mutants as carriers . . . ".

McFarland et al, Microb. Pathog. 3, 129–141, 1987 "Effect of different purine auxotrophic . . . ".

Dougan et al, Mol. Gen. Genet. 207, 402–405, 1987 "Isolation of stable aroA mutants of Salmonella . . . ".

O'Callaghan et al, Infect. Immun. 56, 419–423, Feb. 1988 "Characterization of Aromatic–and Purine–Dependent . . . ".

Dougan et al . Inf. Dis 158, 1329–1335, Dec. 1988 "Construction and Characterization of Vaccine . . . ".

Pittard, "Biosynthesis of the Aromatic amino Acids:, in *Escherichia Coli and Salmonella typhimurium*", Cellular and Molecular Biology 1987, 368–394.

Tacket et al "Comparison of the Safety and Immunogenicity of aroC aroD and cya crp *Salmonella typhi* Strains in Adult Volunteers", Infection and Immunity 60, 536–541, 1992.

Chatfield et al, Vaccine 7 495–498, 1989 "Live Slamonella as vaccines and carriers of foreign antigenic determinants".

Jones et al Oral vaccination of calves against experimental salmonellosis using a double aro mutant of *Salmonella typhimurium*, Vaccine 9, 29–34, Jan. 1991.

Tacket et al "Clinical acceptability and immunogenicity of CVD 908 *Sallmonella typhi* vaccine strain", Vaccine 10, 443–446, 1992.

Charles, I.G. et al. 1989. Proc. Natl. Acad. Sci. 86:3554–3558.

Hoiseth 1983 Diss. Abs. Int'l 44(2B):413.

Ogino et al. 1982. PNAS, USA 79:5828–32.

Gollub et al. 1967. JBC. 242(22):5323–28.

*Primary Examiner*—Nita Minnifield
*Attorney, Agent, or Firm*—Nixon & Vanderhye, P.C.

[57] ABSTRACT

An attenuated microorganism harboring two mutated genes, each of which is located in the organisms aromatic pathway is provided. These organisms can usefully form the basis of a vaccine. They can be genetically engineered so as to express antigens from other pathogens and thus form the basis of a range of multi-valent vaccines.

23 Claims, 1 Drawing Sheet

VACCINES CONTAINING BACTERIA ATTENUATED BY MUTATIONS IN TWO GENES OF THE AROMATIC AMINO ACID BIOSYNTHETIC PATHWAY

This is a Rule 60 Division of application Ser. No. 08/135,436, filed Dec. 13, 1993, now abandoned, which is a continuation of 07/979,460, filed Nov. 20, 1992 abandoned which is a continuation of 07/857,092 filed Mar. 20, 1992 now abandoned, which is a continuation of 07/642,138 filed Jan. 15, 1991 now abandoned, which is continuation of 07/399,539 filed Aug. 22, 1989, now abandoned.

BACKGROUND OF THE INVENTION

The present invention relates to oral vaccines based on live genetically attenuated microorganisms and to the microorganisms themselves. In particular the invention is directed towards attenuated strains of Salmonella.

In 1950 Bacon et al, (Br. J. Exp. Path. 31: 714–724) demonstrated that certain auxotrophic mutants of *S. typhi* were attenuated in mice when compared with the parental strain. Certain of these strains included mutations in the aromatic and purine biosynthetic pathway. It is also known that other mutations, such as thy A, attenuate bacteria.

In 1981 Hosieth and Stocker (Nature 241: 238–39) reported the construction of an *S. typhimurium* aro A mutant. The aro A mutation was constructed using transposon Tn 10 mutagenesis to construct *S. typhimurium* strains carrying non-reverting lesions in the aro A gene. This gene encodes the enzyme 5-enolpyruvylshikimate-3-phosphate synthase, a key enzyme in the organism's aromatic bio-synthetic pathway, which is absent in mammals. Aro A mutants are therefore dependent on exogenous aromatic compounds, including the aromatic amino acids, p-amino benzoic acid and 2,4, dihydroxybenzoate for growth. It was shown in in-bred mice that *S. typhimurium* aro A mutants are attenuated in and were found to be effective live vaccines in mice against murine salmonellosis when delivered orally or parenterally.

If a microorganism is to be used in a live form in a vaccine preparation, safety reasons dictate that the microorganism be attenuated with at least two mutations, preferably in separate parts of the genome. It is clearly important that such a microorganism does not revert back to the virulent parent. The probability of this happening with a single mutation is considered to be small. However, the risk of reversion occurring in a strain harbouring mutations in two discrete genes, located in different places In the genome, is insignificant. A double mutant of this sort is thus considered to be a much safer candidate for use in a vaccine.

In European Patent Application Publication No. 184086 (The Board of Trustees of the Leland Stanford Junior University; Inventor: Bruce Stocker) there is described the construction of a non-reverting strain of *S. typhi* which harbours aro A and pur A non-reverting mutations. Non-reverting mutations are those mutations which cannot be repaired in a single step. Genetic mutations of this sort include inversions and deletions of a DNA sequence which makes up part of a gene.

In our experiments we have shown that intravenous administration of non-reverting aro A pur A mutants of *S. typhimurium* performed poorly in protecting BALB/c mice against intravenous challenge. These mutants were also shown to be ineffective in protecting BALB/c mice when administered by the oral route. (O'Callaghan et al., 1988 Infect.Immune 56, 419–423).

The aro A and pur A mutations can be prepared using transposons. These are DNA sequences of between 750 base pairs to many thousands of nucleotide pairs which can integrate their genetic material into different positions within the bacterial chromosome. Some transposons encode a gene which will confer antibiotic resistance on the organism containing the transposon. When the insertion occurs within a locus, the continuity of the gene is often interrupted and this results in the loss of gene function. At a frequency of about $10^{-8}$/cells/generation transposons are precisely deleted from the gene. This restores gene function; more frequently however, imprecise excision occurs. This does not restore gene function and often leads to a non-reverting mutation.

Some of the work carried out in support of this application is centered on *S. typhi*, the cause of human typhoid. *S. typhi* is essentially a human pathogen and thus is not suitable for most animal experimental work. Animal studies are carried out using a mouse model and the organism *S.typhimurium*, a closely related organism which causes a "typhoid-like" disease in mice and cattle. A description of this mouse model can be found in Collins, 1974, Bacteriol Rev. 38, 371.

For a microorganism to be considered for use in a vaccine, it must exhibit the following properties:—

I) Sufficiently attenuated such that it substantially fails to cause the infection associated with the unattenuated microorganism;

II) substantially incapable of reversion to virulence,

III) capable of inducing immunity in an animal inoculated with the organism and thus providing protection against subsequent challenge with the virulent strain.

It is believed that the live microorganisms described in the prior art for use as vaccines have failed to fulfil all the necessary criteria noted above. Nevertheless, the desirability to develop a live vaccine which avoids the short comings of the prior art remains, since it has been shown (Collins, Bacteriol Rev. 1974) that generally live bacteria have greater immunizing efficacy than killed bacteria. The present inventors have shown that introduction of a non-reverting mutation into each of two discrete genes in the aromatic pathway of a bacterium provide a suitable organism for use in a live vaccine preparation.

SUMMARY OF THE INVENTION

Thus according to a first aspect of the invention there is provided a attenuated microorganism harbouring a non-reverting mutation in each of two discrete genes in its aromatic biosynthetic pathway. The microorganism is preferably a bacteria.

DETAILED DESCRIPTION OF THE PREFERRED EMBODIMENTS

Figure 1:
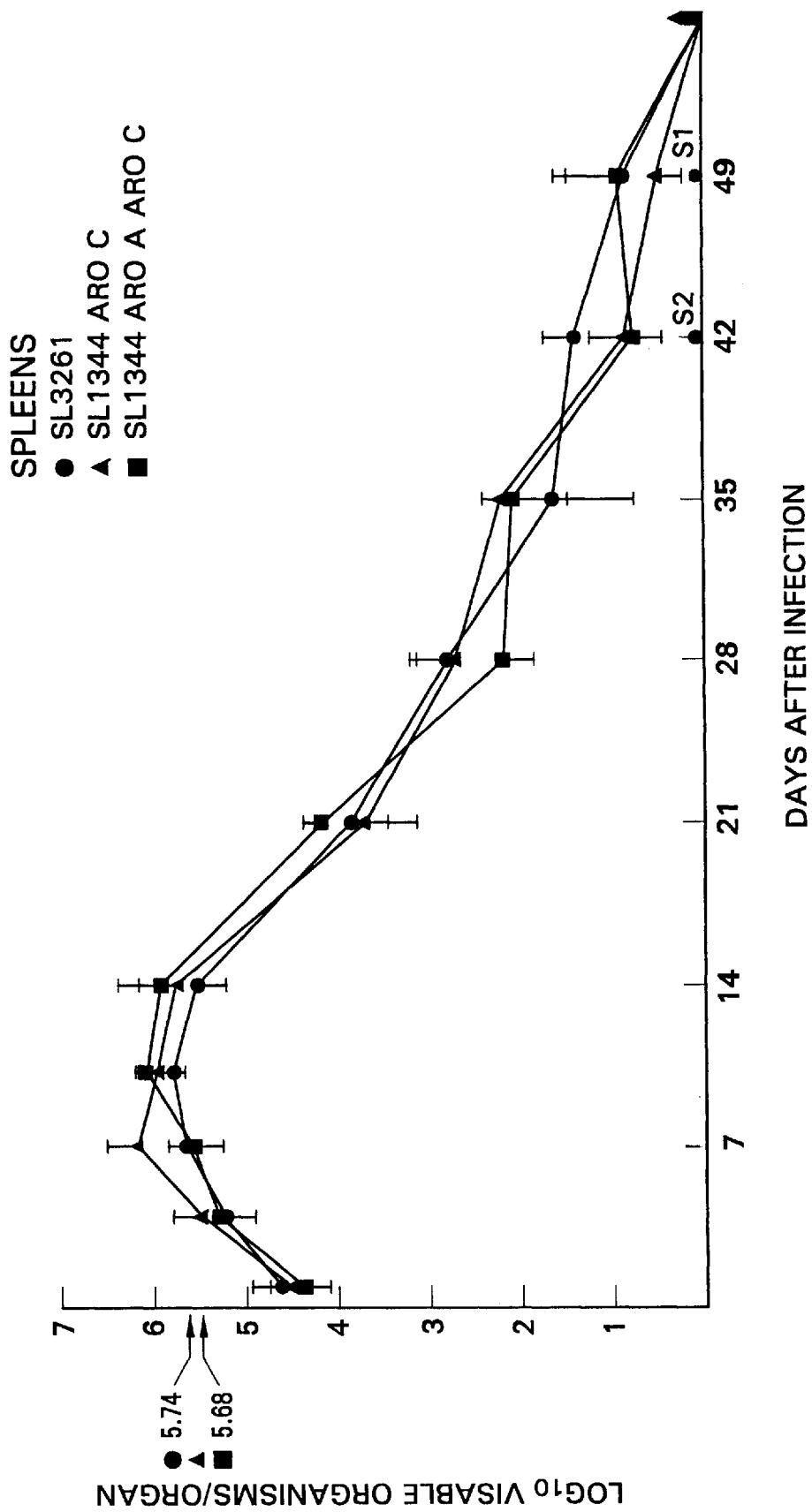
FIG. 1 illustrates the persistance of *S. typhimurium* SL 3261, SL 1344 aro C and SL 1344 aro A aro C in the spleens of mice. Log 10 viable organisms/organ is plotted against days after infection.

There are at least ten genes involved in the synthesis of chorismate, the branch point compound in the aromatic amino acid biosynthetic pathway. Several of these map at widely differing locations on the bacterial genome ie, aro A (5-enolpyruvylshikimate-3-phosphate synthase) aro C (chorismate synthase) aro D (3-dihydroquinate dehydratase) and aro E (shikimate dehydrogenase).

Thus in preferred embodiments of the present invention one of the mutations occurs in the aro A, aro C, aro D or aro E genes. In three embodiments, the invention provides aro A aro E mutant bacteria, aro A aro C mutant bacteria and aro A aro D mutant bacteria although other double aro mutants are within the scope of the present invention.

In particular this work can be extended to a whole range of bacterial pathogens (especially those bacteria which invade and grow within eucaryotic cells or colonise muscosal surfaces). Examples of these include members of the genera Salmonella, Bordetella, Haemophilus, Leptospira and Streptococcus, eg. *S.typhi*, the cause of human typhoid; *S.typhimurium* the cause of salmonellosis in several animal species; *S.enteritidis* a cause of food poisoning in humans; *S.cholerasuis*, the cause of salmonellosis in pigs; *Bordetella pertussis* the cause of whooping cough; *Haemophilus influenzae*, a cause of meningitis; *Mycobacterium tuberculosis*, the cause of tuberculosis and *Neisseria gonorrhoeae* the cause of gonorrhoea, *Yersinia pestio*, the cause of bubonic plague.

In a preferred embodiment of the invention there is provided a *S. typhi* strain Ty 2 harbouring either aro A aro C or aro A aro E or aro A aro D non-reverting mutations.

The construction of *S. typhi* Ty 2 aro A is documented in MGG 207, 402 (Dougan et al). Non reverting mutations were generated by transducing an LT2 aro A:: Tn 10 marker into *S. typhi* Ty 2 strain. Tn 10 transposon carries a gene encoding for tetracycline resistance. Transductants are selected that are tetracycline resistant by growing colonies on an appropriate medium. Further selection is undertaken by screening for those organisms which have lost the tetracycline resistance gene and which are also aromatic dependent.

An alternative method for introducing a deletion into the *S.typhi* aro A gene (or other *S.typhi* aro genes) involves transposon mutagenesis of a cloned *S.typhi* aro A gene, recombination of the mutated gene into the *S.typhi* chromosome replacing the wild-type gene with the mutant and selection for imprecise exision of the transposon. This method eliminates the introduction of non *S.typhi* DNA into the vaccine strain.

In principle there are several ways of introducing the second mutation into the second gene. One method involved the insertion of a transposable element into the second gene and then relying on its imprecise excision by the bacterium in the same manner as described above for constructing the first mutation. The introduction of a mutation into a second aro gene produces a double aro mutant. This is phenotypically indistinguishable from a single aro mutant. Thus to complement the first mutated aro gene, a cloned non mutated copy of one of the genes is introduced on a plasmid into the organism and the organism checked for aromatic compound dependence using the appropriate selection medium.

Another method involves cloning the second gene into a vector eg a plasmid or cosmid, and then incorporating a selectable marker gene into the cloned second gene at the same time inactivating that gene. A plasmid carrying the inactivated gene and a different selectable marker can be introduced into the organism by known techniques. It is then possible by suitable selection to identify a mutant wherein the inactivated gene has recombined into the organism's own chromosome and the organisms own copy of the gene has been lost. In particular, the vector used is one which is unstable in the organism and will be spontaneously lost. The mutated gene on the plasmid and the organisms own copy of the gene on its chromosome maybe exchanged by a genetic cross-over event. Additional methods eliminate the introduction of foreign DNA into vaccine strains at the site of mutations.

The aro A aro C and aro A aro E and aro A aro D mutants of the present invention are sufficiently attenuated to be substantially safe for use in vaccines, and are sufficiently immunogenic to raise an immune response in a patient which will afford the patient protection on subsequent challenge with the virulent strain.

The strains of the present invention may be genetically engineered so as to express antigens from one or more different pathogens. Such pathogens, may be viral, bacterial, protozoal or of higher parasitic organisms. The pathogens may infect both humans and other mammals, but may be species selective, or even species specific. Such strains could then form the basis of a bi or multivalent vaccine. Examples of useful antigens include *E. coli* heat labile toxin B subunit (LT-B) *E. coli* K88 antigens, FMDV (Foot and Mouth) peptides, Influenza viral proteins, 69Kd protein from *B.pertussis*. Other antigens which could be usefully expressed would be those from Chlamydia, flukes, mycoplasma, roundworms, tapeworms, rabies virus and rotavirus.

These antigens may be produced by the introduction of the gene or genes encoding them into expression cassettes. Expression cassettes will include DNA sequences, in addition to that coding for the structural gene, which will encode for transcriptional and translational initiation and termination regions. The expression cassette may also include regulatory regions. Such expression cassettes are well known in the art and it is well within the skill of the skilled man to construct them. The expression cassette may be a construct or a naturally occuring plasmid. An example of a genetically engineered attenuated Salmonella which expresses a foreign antigen can be found in EP Application Publication No. 0 127 153 A (SSVI/Wellcome). The expression cassette may also be engineered to allow the incorporation of the heterologous gene into the bacterial chromosome.

A further bivalent vaccine comprising an attenuated *Salmonella typhi*, capable of expressing the *E.coli* heat-labile enterotoxin subunit B was disclosed by Clements et al (Infection and Immunity, 46, No. 2., Nov. 1984, p564–569). Ty21a has been used to express other antigens such as the *Shigella sonnei* form I antigen (Formal et al, Infection and Immunity 34 746–750).

According to a second aspect of the invention there is provided an attenuated bacterium, as herein described, transformed with an expression cassette encoding an antigen of a pathogen, wherein in use said antigen is expressed by said attenuated bacterium.

According to a third aspect of the invention we provide a pharmaceutical composition which comprises attenuated bacteria as herein described in admixture with a pharmaceutically acceptable carrier. Preferably the pharmaceutical composition is a vaccine composition.

The vaccine is advantageously presented in a lyophilised form, for example in a capsular form, for oral administration to a patient. Such capsules may be provided with an enteric coating comprising for example Eudragate, "S", Eudragate "L", cellulose acetate, cellulose phthalate or hydroxy propylmethyl cellulose. These capsules may be used as such, or alternatively, the lyophilised material may be reconstituted prior to administration, e.g. as a suspension. Reconstitution is advantageously effected in a buffer at a suitable pH to ensure the viability of the organisms. In order to protect the attenuated bacteria and the vaccine from gastric acidity, a sodium bicarbonate preparation is advantageously administered before each administration of the vaccine. Alternatively the vaccine may be prepared for parenteral administration, intranasal administration or intramammary.

The present invention also provides a method for the prophylactic treatment of a bacterial infection which comprises administering to a patient an effective dose of the above described vaccine. The dosage employed in such a method of treatment will be dependent on various clinical factors, including the size and weight of the patient, the type of vaccine formulated. However, for attenuated *S. typhi* a dosage comprising the administration of $10^9$ to $10^{11}$ *S. typhi* organisms per dose is generally convenient for a 70 kg adult human patient.

In the following, examples are provided of experimental details in accordance with the present invention. It will be understood that these examples are not intended to limit the invention in any way.

Construction of *S. typhi* aro A, aro E and aro A, aro C and aro A aro D vaccine strains All strains were constructed using as a starter strain *S. typhi* Ty2 aro A described in detail previously and the subject of Dougan et al, Mol. Gen. Genet, (1987) 207: 402–405.

EXAMPLE 1

*S. typhi* Ty2 aro A aro E

Strain *S. typhimurium* LT2 aro E::Tn10 was obtained from the Salmonella Stock Centre in Calgary. It was originally isolated by J. Roth. Phage P22 was grown on LT2 aro E::Tn10 to prepare a lysate. The P22 phaqe lysate was used to transduce *S. typhi* Ty2 aro A selecting for tetracycline resistance. At this point a plasmid encoding a cloned aroA gene. from *S. typhimurium* C5 to complement the aro A mutation was introduced into the *S. typhi* aro A strain. *S. typhi* aro A, aro E::Tn10 carrying the cloned aro A gene was phenotypically dependent on the aromatic compounds (normally required aro mutants). The Tn 10 element was removed from the aro E gene by selecting tetracycline sensitive variants on Bochner medium, a technique used previously (Bochner et al, J. Bacteriol, 143, 929–933). *S. typhi* aro A aro E mutants harbouring the cloned aro A gene were checked for aromatic dependence using minimal medium. Aromatic dependent colonies were selected and checked extensively for aro E reversion, by plating $10^{11}$ organism on minimal medium lacking aromatic compounds and incubating the medium at 37° C. and checking over five days for revertant colonies. Colonies which were stably aro E despite exhaustive screening were propagated to select variants which had spontaneously lost the cloned aro A gene. One *S. typhi* aro A aro E mutant was selected. This has been deposited at the National Collection of Type Cultures, 61 Colindale Avenue, London NW9 5HT under accession No. 12164, dated Nov. 25, 1987, in accordance with the terms of the Budapest convention.

EXAMPLE 2

*S. typhi* Ty2 aro A aro C

Strain *S. typhi* Ty2 aro A was used as a starter strain. The aro C gene of *S. typhi* Ty2 was cloned using cosmids to complement *E. coli* aro C using the methods of Hohn and Collins (Gene 11: 291–298 (1978)). The aro C cosmid was subjected to transposon Tn 5 mutagenesis and subcloned to locate a small DNA fragment encoding the cloned aro C gene. The cloned aro C gene was inactivated by cloning a Mercury metal resistance gene into the coding region for aro C. A plasmid carrying the inactivated aro C was introduced into *S. typhi* aro A. This plasmid also contains a gene for ampicillin resistance. By selecting for mercury resistance and ampicillin sensitivity it was possible to identify a mutant wherein an inactivated aro C had recombined into the *S. typhi* chromosome to generate an *S. typhi* aro A aro C mutant.

An alternative construct has been made which involved the use of a Kanamycin resistance gene (Km-R), in place of the mercury metal resistance gene.

The *S. typhi* Ty2 aro A aro C Km-R has been deposited at the National Collection of Type Cultures, 61 Colindale Avenue, London NW9 5HT under accession No. 12165, dated Nov. 25, 1987, in accordance with the terms of the Budapest convention.

EXAMPLE 3:

Construction of a *Salmonella typhi* aroA aroD double mutant

*S.typhi* aro A was used as the starter strain. Construction of the *S.typhi* aro A aro D was achieved by transducing the strain with a P22 phage lysate prepared using donor strain LT2 aro D553::Tn10 and selecting for tetracyline resistance. One isolate was purified and used to prepare tetracyline sensitive derivatives by selection on Bochner medium. Several of these were purified and transformed with plasmid pAB51 (aroA$^+$) to complement the aro A deletion. One of the tetracyline sensitive isolates that was stably aromatic compound dependent when harbouring this plasmid was designated *S.typhi* Ty2 aro A aro D.

All the *S.typhi* strains constructed harbouring mutations in different aro genes still produced Vi antigen, were '0' inagglutinable, 09 agglutinable following boiling and were of flagella type Hd. One such aro A aro D strain has been deposited at the National Collection of Type Cultures, 61 Colindale Avenue, London, under no. NCTC 122309, dated Dec. 15, 1988, in accordance with the terms of the Budapest convention.

EXAMPLE 4:

Construction of double aro mutants in *S.typhimurium, S.dublin*, and *S.cholerasuis*.

An aro A deletion was introduced into *S.typhimurium* SL1344, *S.dublin, S.cholerasuis* using the method of McFarland and Stocker. A phage lysate prepared from strain TT472 was used to transduce all the Salmonella strains, selecting for tetracycline-resistant colonies. Strain TT472 carries Tn 10 inserted within ser C which is upstream of and within the same operon as aro A. Tetracycline-resistant transductants were aromatic compound, serine and pyridoxine dependent. A second P22 lysate was prepared, grown on SL5254, which has a known deletion within aro A. This was used to transduce the tetracycline resistant strains which were ser C::Tn10 and transductants were selected on minimal medium lacking serine and pyridoxine but containing aromatic compounds. Colonies growing on minimal medium with added aromatic compounds but in the absence of serine and pyridoxine were tetracycline-sensitive and aromatic compound dependent.

EXAMPLE 4a:

Construction of *S.typhimurium* aro A aro C.

*S.typhimurium* aro A aro C was constructed by first moving a stable aro C mutation from the avirulent *S.typh-* imurium strain SA2018 into the mouse-virulent *S.typhimurium* strain SL1344 using the following series of transductions. A P22-transducing lysate prepared using *S.typhimurium* strain SGSC592 zei608::Tn10 was used to transduce Tn 10 into strain SA2018. The Tn 10 in strain SGSC592 is 40% linked to the wild type aro C gene, whereas strain SA2018 harbours a stable aro C mutation. Tetracycline resistant transductants were picked onto minimal medium and several colonies were found to be aromatic dependent. One of these isolates was purified and used to prepare a second P22 phage lysate. This lysate was used to transduce *S.typhimurium* SL1344 and again several tetracycline-resistant, aromatic compound-dependent transductants were identified. One isolate was used to prepare tetracycline sensitive derivatives by selection on Bochner medium. One tetracycline-sensitive aromatic compound dependent isolate was purified and an aro A deletion introduced into it using the method of McFarland and Stocker as described previously. To confirm that this isolate was aro A aro C it was transformed with either plasmid pAB51 (aro $A^+$) or pTMC12H (aro $C^+$) and was found to be aromatic compound dependent when it harboured either of these plasmids.

EXAMPLE 4b:

Construction of *S.typhimurium* aro A aro D

*S.typhimurium* aro A aro D was constructed by introducing an aro D deletion into the SL1344 aro A strain. This was achieved by transducing the strain with a P22 phage lysate prepared using donor strain LT2 aro D553::Tn10 and selecting for tetracycline resistance. One isolate was purified and used to prepare tetracycline-sensitive derivatives by selection on Bochner medium. Several of these were purified and transformed with plasmid pAB51 (aro $A^+$) to complement the aro A deletion. One of the tetracycline-sensitive isolates that was stably aromatic compound dependent when harbouring this plasmid was designated SL1344 aro A aro D.

EXAMPLE 4c:

Construction of *S.typhimurium* aro A aro E

*S.typhimurium* aro A aro E was constructed by introducing an aro E deletion into the SL1344 aro A strain. This was achieved by transducing the strain with a P22 phage lysate prepared using donor strain LT2 aro E::Tn10 and selecting for tetracycline resistance. One isolate was purified and used to prepare tetracycline sensitive derivatives by selection on Bochner medium. Several of these were purified and transformed with plasmid pAB51 (aro $A^+$) to complement the aro A deletion. One of the tetracycline-sensitive isolates that was stably aromatic compound dependent when harbouring this plasmid was designated SL1344 aro A aro E.

EXAMPLE 5:

*S.dublin* and *S.cholerasuis* aro A aro D derivatives were constructed in the same way as the SL1344 aro A aro D derivative as shown in Example 4b.

In vivo properties of attenuated *S.typhimurium* strains

Details of the *S. typhimurium* stains used in this work are shown in Table 1.

Infection of mice and enumeration of bacteria in murine organs

To determine the number of organisms in various organs after tnt i.v. inoculation of *S. typhimurium*, liver and spleens were homogenised as described in Hormaeche, CE, Immunology, 37, 311–318. Viable counts were performed on these homogenates using L-agar as growth medium and are expressed in FIG. 1 as geometric means ± two standard errors of the mean, for four mice per point.

Innately Salmonella susceptible BALB/c mice of 8–10 weeks of age were used throughout examples 6, 7 and 8. The intravenous (i.v.) $LD_{50}$ for virulent strains was obtained by injecting groups of 5 mice with serial ten fold dilutions, prepared in phosphate buffered saline pH 7.2 (PBS), of overnight L-broth cultures harvested by centrifugation and resuspended in PBS to give a concentration of $10^9$–$10^{11}$ bacteria per ml. This was serially ten fold diluted in PBS, the top dose being 0.2 ml of the neat suspension given i.v. or orally with 8–10 mice per group. Deaths were recorded over the following four weeks and the $LD_{50}$ was calculated using the method of Reed and Muench, Am. J. Hyg. 27: 493–497 (1983). For i.v. inoculation mice were injected with 0.2 ml of bacterial suspension into the tail vein. For oral inoculation bacteria were administered in 0.2 ml volumes to lightly ether anaesthetised mice by gavage as described previously (Microbial Pathogenesis 2: 211–221).

EXAMPLE 6.

Attenuation of virulent *S. typhimurium* strains by the introduction of a stable aro mutations and other auxotrophic mutations.

*S. typhimurium* HWSH and SL1344 are both mouse virulent strains with an $LD_{50}$ of less than 10 organisms following i.v. challenge in BALB/c mice. Intravenous $LD_{50}$s were determined for selected auxotrophic derivatives of these strains in BALB/c mice (Table 2). All aro A and pur A mutants were well attenuated compared to the parental strains. HWSH aro A and SL3261 (SL1344 aro A) had $LD_{50}$s of log 7.4 and log 7.1 respectively in good agreement with published data. The pur A and aro A pur A derivatives were even more attenuated. The HWSH pur E strain was considerably less attenuated though the measured $LD_{50}$ was found to vary considerably between experiments. For example, sometimes mice given as few as 100 organisms died whereas others given up to $10^4$–$10^5$ organisms survived. The aro C aro A mutant was less attenuated than the aro A pur A mutant having an $LD_{50}$ of 6.5. This figure was the same for the single aro C mutant. Orally, aromatic or purine mutants did not kill the mice even when doses as high as $10^{10}$ organisms were given.

EXAMPLE 7

Persistance of *S.typhimurium* single and double aro mutants after i.v. inoculation of BALB/c mice.

All *S.typhimurium* strains exhibited a very similar pattern of persistence, with no salmonellae detectable in spleens by day 56 (FIG. 1).

Attenuated strains of *S.typhimurium* as orally administered vaccines.

EXAMPLE 8

The ability of orally administered auxotrophic *S. typhimurium* strains to protect BALB/c mice against an oral challenge with virulent *S. typhimurium* (SL344) was treated. Mice were initially infected orally with between $10^9$–$10^{10}$ of the auxotrophic mutants and then the immunised mice were challenged orally four weeks later with the parental virulent strain.

The results in Table 3 clearly show that neither pur A nor aro A pur A mutants induced any significant protection against oral challenge whereas the aro A, aro C and aro A aro C mutants did induce significant protection against oral challenge at both 28 and 70 days post immunisation.

EXAMPLE 9:

Formulation

An *S. typhi* organism of the present invention is preferably presented in oral tablet form.

| Ingredient | mg/tablet |
|---|---|
| Core-tablets | |
| 1) Freeze-dried excipient carrier containing $10^9$–$10^{10}$ *Salmonella typhi*. | 70.0 |
| 2) Silica dioxide (Aerosil 200) | 0.5 |
| 3) Dipac (97% sucrose) | 235.0 |
| 4) Cross-linked Povidone (Kollidon CL) | 7.0 |
| 5) Microcrystalllne Cellulose (Avicel pH 102) | 35.0 |
| 6. Magnesium Stearate | 2.5 |
|  | 350.0 |
| Coating | |
| 7) Opadry Enteric, OY-P-7156 | 35.0 |
| (Polyvinyl acetate phthalate + Diethylphthate) | |
|  | 385.0 |

A carrier containing 5% sucrose 1% sodium glutamate and 1% bacto casitone in an aqueous solvent is prepared. *S. typhi* organism are suspended in this carrier and then subjected to freeze-drying.

The freeze-dried material is blended with Aerosil 200 and the blended mixture Is sifted through a screen. The sifted powder is mixed with Dipac, Kollidan CL, Avicel pH 102 and Magnesium Stearate in a blender. This blend is compressed into tablets for subsequent enteric coatings.

The skilled man will appreciate that many of the ingredients in this formulation could be replaced by functionally equivalent pharmaceutically acceptable excipients.

TABLE 1

Strains of *S. typhimurium* used in this study.

| Strain | Auxotrophy |
|---|---|
| SL1344 | his |
| SL3261 | aro A his |
| SL1344 pur A | pur A his |
| SL3261 pur A | pur A aro A his |
| SL1344 | aro C |
| SL1344 | aro A |
| SL1344 | aro A aro C |
| HWSH* | Prototroph |
| HWSH aro A | +e,uns aro A |
| HWSH pur A | pur A |
| HWSH aro A pur A | aro A pur A |
| HWSH pur E | pur E |
| C5 | Prototroph |

*A mouse-virulent, calf-virulent strain isolated from a calf dying of Salmonellosis.

TABLE 2

Log $LD_{50}$ values obtained by infecting BALB/c mice i.v. with various auxotrophic derivatives of two highly virulent *S. typhimurium* strains[a].

|  | Log $LD_{50}$ |  | Log $LD_{50}$ |
|---|---|---|---|
| SL1344 | <1 | HWSH | <1 |
| SL3261 | 6.9 | HWSH aro A | 7.4 |
| SL1344 pur A | 6.7 | HWSH pur A | 8.6 |
| SL3261 pur A | 8.7 | HWSH aor A pur A | 8.9 |
| SL1344 aro C | 6.7 | HWSH pur E | 3.8 |
| SL1344 aro C aro A | 6.5 | | |
| SL1344 aro A | 6.75 | | |

[a]All $LD_{50}$s were calculated after 28 days, except for HWSH pur E, calculated after 56 days.

TABLE 3

| Immunising strain | Challenge Day 28 | Challenge Day 70 |
|---|---|---|
| SL1344 pur A | 6.7 | ND |
| SL3261 pur A | 5.6 | ND |
| Unimmunised | 6.2 | ND |
| SL3261 | >10.1 | 9.1 |
| SL1344 aro C | >10.1 | >9.9 |
| SL1344 aro A aro C | >10.1 | >9.9 |
| Unimmunised | 7.4 | 6.7 |

Note:
SL 3261 is aro A

We claim:

1. A vaccine comprising a pharmaceutically acceptable excipient and a bacterium which is sufficiently attenuated such that it fails to cause a disease caused by the unattenuated bacterium, but which induces immunity in a mammal inoculated with the bacterium and provides protection against subsequent challenge with a virulent bacterium, wherein attenuation is attributable to a defined, non-reverting mutation in each of two discrete aro genes of the aromatic amino acid biosynthetic pathway.

2. A vaccine as claimed in claim 1 wherein the bacterium has no uncharacterised mutations in the genome thereof.

3. A vaccine as claimed in claim 1 wherein one of the non-reverting mutations occurs in the aroA gene.

4. A vaccine as claimed in claim 3 wherein a second non-reverting mutation occurs in a gene selected from the group consisting of the aroC and aroE genes.

5. A vaccine as claimed in claim 1 wherein the bacterium is selected from the group consisting of the genera Salmonella, Bordetella and Haemophilus.

6. A vaccine as claimed in claim 5 wherein the bacterium is *S. typhi*.

7. A vaccine as claimed in claim 6 wherein the bacterium harbours non-reverting mutations selected from the group consisting of aroA aroC mutations and aroA aroE mutations.

8. A vaccine as claimed in claim 6 wherein the bacterium is a strain of *S. typhi* as deposited under the National Collection of Type Cultures' Accession No. 12164 or 12165.

9. A vaccine as claimed in claim 1 wherein the bacterium expresses a heterologous antigen.

10. A vaccine as claimed in claim 9 wherein the bacterium contains an expression cassette having a DNA sequence encoding an antigen of a pathogen.

11. A vaccine as claimed in claim 1 adapted for oral administration.

12. A vaccine as claimed in claim 1 which induces immunity in a human inoculated with the vaccine.

13. A method of effecting the prophylactic treatment of a bacterial infection, which method comprises administering to a mammal in need of said treatment an effective amount of a bacterium which is sufficiently attenuated such that it fails to cause a disease caused by the unattenuated bacterium, but which induces immunity in the mammal and provides protection against subsequent challenge with a virulent bacterium, wherein attenuation is attributable to a defined, non-reverting mutation in each of two discrete aro genes of the aromatic amino acid biosynthetic pathway.

14. A method as claimed in claim 13 wherein the bacterium has no uncharacterised mutations in the genome thereof.

15. A method as claimed in claim 13 wherein one of the non-reverting mutations occurs in the aroA gene.

16. A method as claimed in claim 15 wherein a second non-reverting mutation occurs in a gene selected from the group consisting of the aroC and aroE genes.

17. A method as claimed in claim 13 wherein the bacterium is selected from the group consisting of the genera Salmonella, Bordetella and Haemophilus.

18. A method as claimed in claim 17 wherein the bacterium is *S. typhi*.

19. A method as claimed in claim 18 wherein the bacterium harbours non-reverting mutations selected from the group consisting of aroA aroC mutations and aroA aroE mutations.

20. A method as claimed in claim 18 wherein the bacterium is a strain of *S. typhi* as deposited under the National Collection of Type Cultures' Accession No. 12164 or 12165.

21. A method as claimed in claim 13 wherein the bacterium expresses a heterologous antigen.

22. A method as claimed in claim 21 wherein the bacterium contains an expression cassette having a DNA sequence encoding an antigen of a pathogen.

23. A method as claimed in claim 13 wherein the mammal is a human.

* * * * *